(12) United States Patent
DeBlasio

(10) Patent No.: US 10,670,556 B2
(45) Date of Patent: Jun. 2, 2020

(54) ELECTROCHEMICAL GAS SENSOR BIASING MODULE

(71) Applicant: TELEDYNE DETCON, INC., Thousand Oaks, CA (US)

(72) Inventor: Nicholas Anthony DeBlasio, Monroe, NC (US)

(73) Assignee: Teledyne Detcon, Inc., Thousand Oaks, CA (US)

( * ) Notice: Subject to any disclaimer, the term of this patent is extended or adjusted under 35 U.S.C. 154(b) by 548 days.

(21) Appl. No.: 15/311,331

(22) PCT Filed: May 14, 2015

(86) PCT No.: PCT/US2015/030747
§ 371 (c)(1),
(2) Date: Nov. 15, 2016

(87) PCT Pub. No.: WO2015/175764
PCT Pub. Date: Nov. 19, 2015

(65) Prior Publication Data
US 2017/0074820 A1   Mar. 16, 2017

Related U.S. Application Data

(60) Provisional application No. 61/994,228, filed on May 16, 2014.

(51) Int. Cl.
*G01N 27/416* (2006.01)
*G01N 27/404* (2006.01)
*G01N 33/00* (2006.01)

(52) U.S. Cl.
CPC ......... *G01N 27/416* (2013.01); *G01N 27/404* (2013.01); *G01N 33/007* (2013.01); *G01N 33/0073* (2013.01)

(58) Field of Classification Search
CPC .......... G01N 27/00; G01N 33/00; G01D 3/00; G01D 4/00; G01D 5/00
(Continued)

(56) References Cited

U.S. PATENT DOCUMENTS

2003/0101569 A1* 6/2003 Watanabe .......... G01N 27/4067
29/592.1
2005/0173407 A1* 8/2005 Chen .................... H05B 1/0288
219/490

(Continued)

FOREIGN PATENT DOCUMENTS

| DE | 19847706 A1 | 4/2000 |
|---|---|---|
| JP | 2004069378 A | 3/2004 |
| WO | 2012106275 A1 | 8/2012 |

OTHER PUBLICATIONS

International Search Report and Written Opinion dated Sep. 10, 2015 for International Application Serial No. PCT/US2015/030747, International Filing Date: May 14, 2015, consisting of 6-pages.

*Primary Examiner* — Rexford N Barnie
*Assistant Examiner* — Joseph N Inge
(74) *Attorney, Agent, or Firm* — Christopher & Weisberg, P.A.

(57) ABSTRACT

An electrochemical gas sensor biasing module may include a main housing, a battery that is contained in and/or extending from the main housing, and a sensor connector extending from a portion of the main housing. The sensor connector is configured to removably connect to an electrochemical gas sensor so that energy from the battery is delivered to the electrochemical gas sensor in order to maintain the electrochemical gas sensor in a biased state.

20 Claims, 3 Drawing Sheets

(58) Field of Classification Search
USPC .......................................................... 307/154
See application file for complete search history.

(56) References Cited

U.S. PATENT DOCUMENTS

| | | | |
|---|---|---|---|
| 2008/0169934 A1* | 7/2008 | Lang .................. | G01N 33/0009 340/632 |
| 2009/0314056 A1* | 12/2009 | McCauley ......... | G01N 27/4078 73/23.31 |
| 2010/0134072 A1* | 6/2010 | Neu ........................ | G06F 1/632 320/137 |
| 2013/0018491 A1* | 1/2013 | Kelly ................... | G01N 1/2035 700/90 |
| 2013/0186777 A1* | 7/2013 | Scheffler ................ | G01N 27/26 205/785.5 |
| 2014/0238101 A1* | 8/2014 | Mealy, Jr. ............. | G01N 33/007 73/1.06 |

* cited by examiner

ELECTROCHEMICAL GAS SENSOR BIASING MODULE

CROSS-REFERENCE TO RELATED APPLICATION

This Application is a Submission Under 35 U.S.C. § 371 for U.S. National Stage Patent Application of International Application Number: PCT/US2015/030747, filed May 14, 2015, entitled "ELECTROCHEMICAL GAS SENSOR BIASING MODULE," which claims priority to U.S. Provisional Application No. 61/994,228, filed May 16, 2014, the entirety of both which are incorporated herein by reference.

FIELD OF THE DISCLOSURE

Embodiments of the present disclosure generally relate to systems and methods for biasing or providing power to an electrochemical gas sensor, and, more particularly, to an electrochemical gas sensor biasing module or assembly that is configured to bias or provide power to an electrochemical sensor as the sensor is transported between locations, for example.

BACKGROUND OF THE DISCLOSURE

Electrochemical gas sensors are used to measure concentrations of target gases within particular locations. For example, an electrochemical gas sensor may react with a target gas at an electrode and measure a resulting current. A typical electrochemical gas sensor may include two to four electrodes in contact with an electrolyte, such as mineral acid. The electrodes may be fabricated by fixing a high surface area precious metal on to a porous hydrophobic membrane. The working electrode(s) may be exposed to both the electrolyte and the ambient air to be monitored, such as through a porous membrane. In operation, the target gas diffuses into the sensor, through the porous membrane, to the working electrode(s) where the gas is oxidized or reduced. The resulting electrochemical reaction produces an electric current that passes through an external circuit.

Typically, an electrochemical gas sensor is installed into a gas detection system. Prior to calibration, a certain amount of time is needed for a sensor to stabilize. In short, the sensing medium, such as a sensor kernel, within the sensor needs a sufficient amount of time to warm up before it is able to properly function. For example, before operating to detect gas, a sensing medium needs to be biased or powered for a certain amount of time to warm up. The warm up time may be 5 minutes to 8 hours, depending on the gas being detected. When the warm-up operation takes place in a hazardous area, the area may need to be declassified so that the gas detection system can be opened and the electrochemical gas sensor installed.

Further, if the electrochemical gas sensor is to be removed from the gas detection system and transported to another site, the electrochemical gas sensor typically needs to be warmed up again, such as through a certain amount of power being applied thereto for a certain amount of time, before the sensor may be used with respect to the gas detection system. As noted, however, the warm up time may prevent the sensor from properly functioning for a relatively long period of time.

SUMMARY OF THE DISCLOSURE

Certain embodiments of the present disclosure provide an electrochemical gas sensor biasing module that may include a main housing, a battery contained in or extending from the main housing, and a sensor connector extending from a portion of the main housing. The sensor connector is configured to removably connect to an electrochemical gas sensor so that energy from the battery is delivered to the electrochemical gas sensor in order to maintain the electrochemical gas sensor in a biased state.

The biasing module may also include an intrinsic safety line within an internal chamber of the main housing. The intrinsic safety line may include at least a resistor and a fuse.

The biasing module may also include a low dropout regulator that is configured to output a constant voltage to the electrochemical gas sensor.

The biasing module may also include a switch configured to selectively switch the battery between active and deactivated states. In the active state, power is drawn from the battery. In the deactivated state, power is not drawn from the battery.

DETAILED DESCRIPTION OF THE DISCLOSURE

The foregoing summary, as well as the following detailed description of certain embodiments will be better understood when read in conjunction with the appended drawings. As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
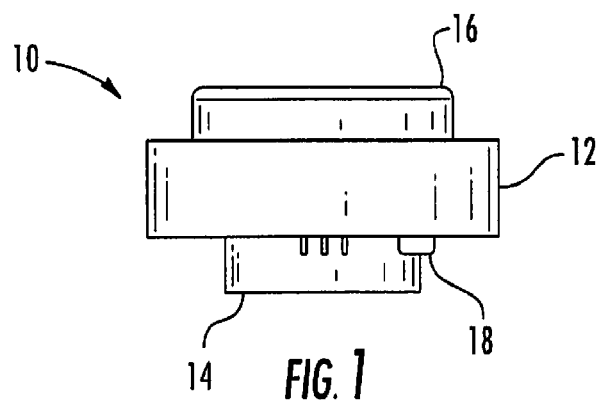
FIG. 1 illustrates a front view of an electrochemical gas sensor biasing module, according to an embodiment of the present disclosure.

FIG. 1 illustrates a front view of an electrochemical gas sensor biasing module 10, according to an embodiment of the present disclosure. The electrochemical gas sensor biasing module 10 is configured to connect to an electrochemical gas sensor to provide a biasing power thereto, so that the electrochemical gas sensor may be transported between locations, for example, and immediately used to detect gas at its relocated position. Because the electrochemical gas sensor biasing module 10 provides a biasing power to (or "biases" or "provides power to") the electrochemical gas sensor, the sensor remains in a full functional state, and does not cool down to a sub-optimal, pre-detecting, or cool state that would otherwise require the electrochemical gas sensor to be warmed up before being used to detect gas.

The bias module 10 may include a main housing 12 that contains electronics, such an intrinsic safety line or circuit and a low dropout regulator, for example. A sensor connector 14 extends from a first end of the main housing 12, while a battery 16 extends from a second end, which is opposite from the first end, of the main housing 12. The sensor connector 14 may be a custom 8 pin connector for example, while the battery 16 may be a lithium ion battery, for example. Alternatively, the battery 16 may be secured to various other portions of the main housing 12. For example, the battery 16 may be contained within the main housing 12. An on/off switch 18 may extend from the main housing 12. The on/off switch 18 is configured to switch the bias module 10 between an active state, in which power from the battery is drawn and supplied to an electrochemical sensor through the connector 14, and a deactivated state, in which battery power is conserved.

In operation, the connector 14 mechanically and electrically connects to a reciprocal feature (such as a receptacle) formed on or in an electrochemical gas sensor. The connector 14 includes contacts, such as pins, that connect to reciprocal contacts of the electrochemical gas sensor. In the active state, power or energy from the battery is provided through the contacts of the connector 14 to the reciprocal contacts of the electrochemical gas sensor so that the electrochemical gas sensor remains in a biased or otherwise powered state.

Figure 2:
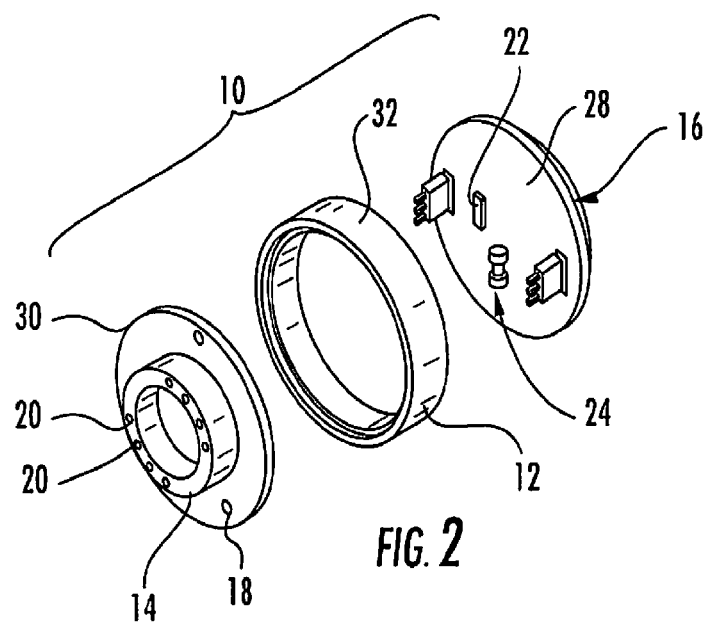
FIG. 2 illustrates a perspective exploded view of an electrochemical gas sensor biasing module from a first end, according to an embodiment of the present disclosure.
Figure 3:
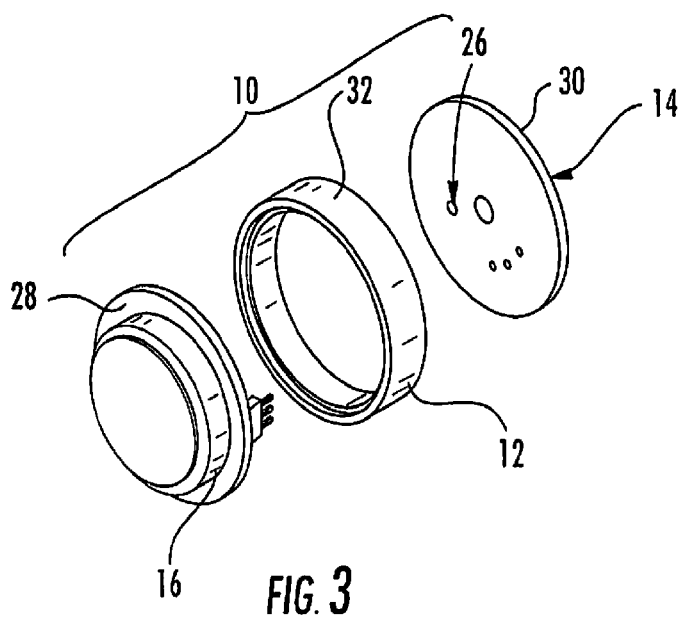
FIG. 3 illustrates a perspective exploded view of an electrochemical gas sensor biasing module from a second end, according to an embodiment of the present disclosure.

FIGS. 2 and 3 illustrate perspective exploded views of the electrochemical gas sensor biasing module 10 from first and second ends, respectively, according to an embodiment of the present disclosure. Referring to FIGS. 2 and 3, one or more electrical contacts 20 may be formed in and/or extend from an outer edge of the connector 14. The main housing 12 may also contain a resistor 22 and a fuse 24 configured to provide an intrinsic safety for the biasing module 10. Additionally, a low dropout regulator 26 may be contained within the main housing 12. The low dropout regulator 26 may be configured to output a constant voltage, such as 2.8V, to a sensor connected to the biasing module 10.

As shown, the battery 16 may be supported on a printed circuit board 28, while the connector 14 may be supported on a printed circuit board 30. The resistor 22 and the fuse 24 may be mounted on the printed circuit board 28, while the low dropout regulator 26 may be mounted on the printed circuit board 30. Interior surfaces of the printed circuit boards 28 and 30 may connect to a circumferential wall 32 to form the main housing 12, such as a plastic mechanical ring 32. Alternatively a plastic cup shaped structure may contain the two printed circuit boards 28, 30 with potting material encasing the printed circuit boards 28, 30 thereby protecting the printed circuit boards 28, 30 for the hazardous location. The interior chamber of the main housing 12 is preferably filled with potting material, for example. While the biasing module 10 is shown having a tube or cylindrical-like structure, the biasing module 10 may be various other sizes and shapes. Also, alternatively, instead of printed circuit boards, the biasing module 10 may include plastic wall panel portions onto which the battery 16 and the connector 14 mount.

Figure 4:
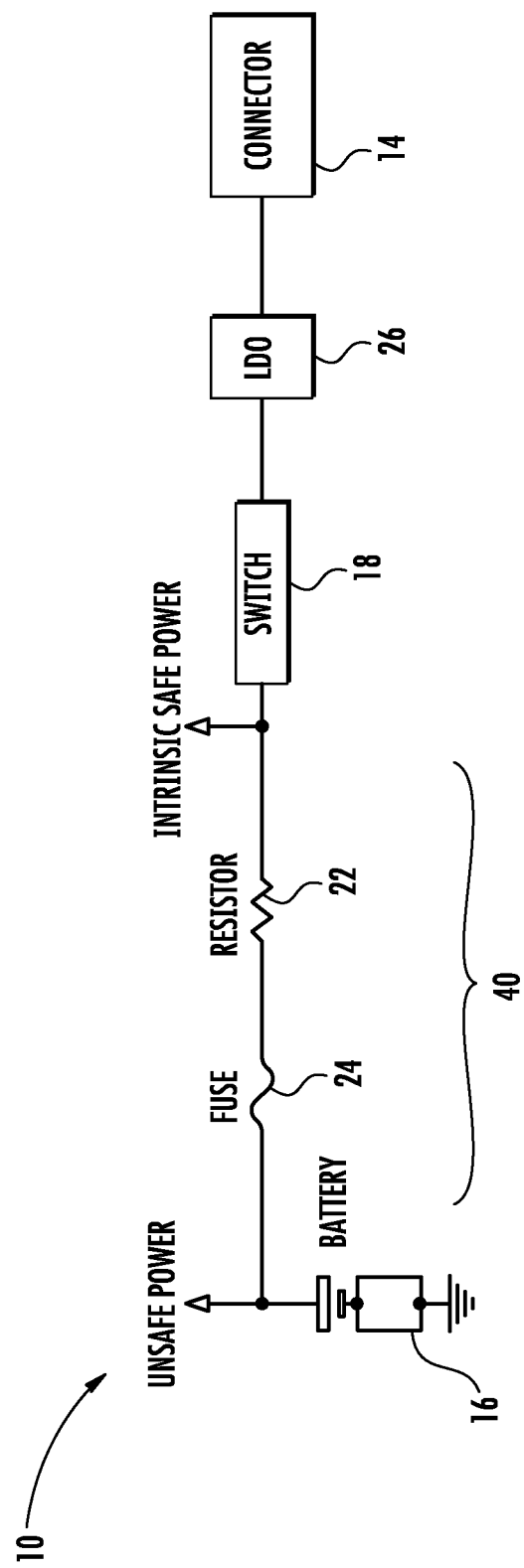
FIG. 4 illustrates an electronic circuit schematic of an electrochemical gas sensor biasing module, according to an embodiment of the present disclosure.

FIG. 4 illustrates an electronic circuit schematic of the electrochemical gas sensor biasing module 10, according to an embodiment of the present disclosure. The resistor 22 and the fuse 24 are part of an intrinsic safety line or circuit 40 that limits the amount of power delivered from the battery 16 so that a spark cannot be generated that could otherwise ignite a hazardous gas. The intrinsic safety line 40 may be a barrier circuit that is configured to limit a current surge and/or continuous current. For example, without the intrinsic safety line 40, if the battery 16 is damaged, such as by being dropped, the force of the drop or damage could cause a spark. However, the intrinsic safety line 40, including the resistor 22 and the fuse 24, shorts the circuit to prevent the spark.

Figures 5, 6:
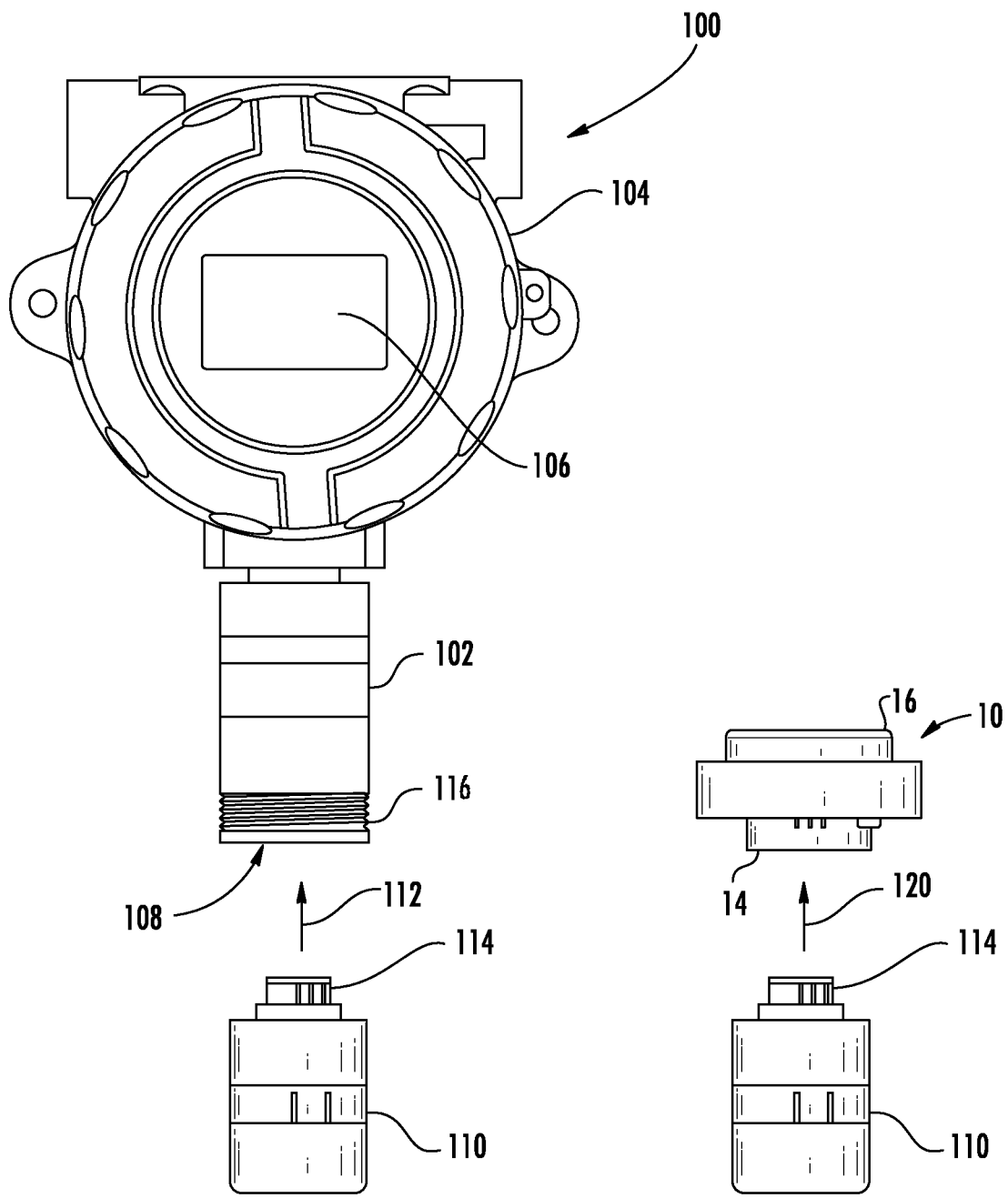
FIG. 5 illustrates a front view of a gas detection system, according to an embodiment of the present disclosure.
FIG. 6 illustrates a front view of an electrochemical gas sensor biasing module disconnected from an electrochemical gas sensor, according to an embodiment of the present disclosure.

FIG. 5 illustrates a front view of a gas detection system 100, according to an embodiment of the present disclosure. The gas detection system 100 includes a gas detector head 102 connected to a transmitter 104, which may include a display 106. The gas detector head 102 may be a tubular member having an internal chamber 108 that is configured to receive an electrochemical sensor 110. The electrochemical sensor 110 is urged into the internal chamber 108 in the direction of arrow 112, such that contacts 114 mechanically and/or electrically engage reciprocal contacts within the internal chamber 108. Once the electrochemical sensor 110 is secured within the internal chamber 108, an end cap (not shown) may be threadably secured to a distal threaded end 116 of the gas detector head 102.

FIG. 6 illustrates a front view of the electrochemical gas sensor biasing module 10 disconnected from the electrochemical gas sensor 110, according to an embodiment of the present disclosure. Referring to FIGS. 5 and 6, when the electrochemical gas sensor 110 is removed from the gas detection system 100, the electrochemical gas sensor 110 may mechanically and electrically mate with the biasing module 10, such as through a connection direction denoted by arrow 120 that causes the contacts 114 to mate with the contacts of the connector 14. Accordingly, power from the battery 16 may then be delivered to the electrochemical gas sensor 110 in order to keep the electrochemical gas sensor 110 in a biased or otherwise powered stated.

As described above, embodiments of the present disclosure provide an electrochemical gas sensor biasing module that is configured to provide power to an electrochemical gas sensor in order to bias a sensor kernel to keep it warm while being transported through a hazardous location before the electrochemical gas sensor is installed into a gas detection system.

The biasing module may be configured to provide a constant power (such as through a low dropout regulator, for example) to the electrochemical gas sensor before the sensor is installed into a gas detection system. The intrinsic safety line may ensure that the module meets various hazardous location approvals.

The biasing module may be configured to be "hot swappable." It is frequently desirable to "hot swap" an electrochemical gas sensor during use (for example, replacing the sensor without declassifying the hazardous area). The biasing module allows the sensor to be transported in a powered state so that the sensor kernel is biased. Prior to installation into the gas detection system, the biasing module may be removed and the sensor installed into the gas detection system without declassifying the hazardous area.

Example 1

A technician attaches a bias module to an electrochemical sensor while in a non-hazardous area. The bias module applies power to the electrochemical sensor in turn powering the conditioning circuit inside. This conditioning circuit applies the appropriate operating bias voltage to the sensor kernel so that it is ready to detect gas. An electrochemical sensor installed in a gas detection system has malfunction. The technician takes the new sensor with the bias module connected into the hazardous area. Without declassifying the area and turning off power to the gas detection system, the technician removes the end cap, unplugs the old sensor, removes the bias module from the new sensor and installs the new sensor into the gas detection system and re-installs the end cap. This process is allowed due to bias module and sensor passing the intrinsic safety approvals process. The technician returns to the safe area with the old sensor and bias module.

Example 2

A technician attaches the bias module to a new electrochemical sensor while in a non-hazardous area. An electrochemical sensor installed in a gas detection system has malfunction. The technician takes the new sensor with the bias module connected into the hazardous area. While walking in the hazardous area, the technician accidently drops the bias module and sensor. The technician picks up the assembly and continues on his way. The bias module and sensor are OK due to testing done during the approvals process. Without declassifying the area and turning off power to the gas detection system, the technician removes the end cap, unplugs the old sensor, removes the bias module from the new sensor and installs the new sensor into the gas detection system and re-installs the end cap. The technician returns to the safe area with the old sensor and bias module.

Example 3

A technician attaches multiple new electrochemical sensors to a bias module in a non-hazardous area. The technician takes the new sensors and the bias module assembly into the hazardous area. Without declassifying the area and turning off power to the gas detection system, the technician removes the end cap, unplugs the old sensor, removes a new sensor from the bias module and installs the new sensor into the gas detection system and re-installs the end cap. This process is allowed due to bias module and sensor passing the intrinsic safety approvals process. The technician travels to the next gas detection system and repeats the process of removing and installing the sensor. At the end, the technician returns to the safe area with the old sensors and bias module.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An electrochemical gas sensor biasing module that is configured to be removably connected to an electrochemical gas sensor, the electrochemical gas sensor biasing module comprising:
a main housing having a first portion and a second portion;
a battery at least partially within the first portion of the main housing, the battery being configured to deliver a biasing power to the electrochemical gas sensor and to maintain the electrochemical gas sensor in a biased state when the electrochemical gas sensor biasing module is removably connected to the electrochemical gas sensor and the electrochemical gas sensor is unattached from a gas detector head; and
a sensor connector at least partially within the second portion of the main housing.

2. The electrochemical gas sensor biasing module of claim 1, wherein the main housing includes an internal chamber, the electrochemical gas sensor further comprising an intrinsic safety line within the internal chamber of the main housing, the intrinsic safety line being in communication with the battery and being configured to limit an amount of power delivered from the battery.

3. The electrochemical gas sensor biasing module of claim 2, wherein the intrinsic safety line includes a resistor and a fuse.

4. The electrochemical gas sensor biasing module of claim 1, further comprising a low dropout regulator in communication with the battery and the sensor connector.

5. The electrochemical gas sensor biasing module of claim 4, wherein the low dropout regulator is configured to output a constant voltage to the electrochemical gas sensor when the electrochemical gas sensor biasing module is connected to the electrochemical gas sensor.

6. The electrochemical gas sensor biasing module of claim 1, further comprising a switch in communication with the battery, the switch being configured to selectively transition the electrochemical gas sensor biasing module between an activated state and a deactivated state.

7. The electrochemical gas sensor biasing module of claim 6, wherein the battery is configured to supply power to the sensor connector when the electrochemical gas sensor biasing module is in the activated state.

8. The electrochemical gas sensor biasing module of claim 1, further comprising a first printed circuit board and a second printed circuit board, the battery being coupled to the first printed circuit board and the sensor connector being coupled to the second printed circuit board.

9. The electrochemical gas sensor biasing module of claim 8, wherein at least a portion of the battery extends from the first portion of the main housing.

10. The electrochemical gas sensor biasing module of claim 1, wherein at least a portion of the sensor connector extends from the second portion of the main housing.

11. An electrochemical gas sensor biasing module, the electrochemical gas sensor biasing module being configured to be removably connected to an electrochemical gas sensor, the electrochemical gas sensor biasing module comprising:
a main housing having a first end and a second end opposite the first end;
a battery at least partially within the main housing first end, the battery being configured to deliver a biasing power to the electrochemical gas sensor and to maintain the electrochemical gas sensor in a biased state when the electrochemical gas sensor biasing module is removably connected to the electrochemical gas sensor and the electrochemical gas sensor is unattached from a gas detector head; and
a sensor connector at least partially within the main housing second end.

12. The electrochemical gas sensor biasing module of claim 11, further comprising an intrinsic safety circuit in communication with the battery, the intrinsic safety circuit being configured to limit an amount of power from the battery to the sensor connector.

13. The electrochemical gas sensor biasing module of claim 12, wherein the intrinsic safety circuit includes a resistor and a fuse.

14. The electrochemical gas sensor biasing module of claim 11, further comprising a first printed circuit board within the main housing first end and a second printed circuit board within the main housing second end, the battery being coupled to the first printed circuit board and the sensor connector being coupled to the second printed circuit board.

15. The electrochemical gas sensor biasing module of claim 11, further comprising a low dropout regulator in communication with the battery and the sensor connector, the low dropout regulator being configured to output a constant voltage through the sensor connector to the electrochemical gas sensor.

16. The electrochemical gas sensor biasing module of claim 11, further comprising a switch in communication with the battery, the switch being configured to selectively transition the electrochemical gas sensor biasing module between an activated state and an deactivated state, the battery being configured to deliver a biasing power to the electrochemical gas sensor when the electrochemical gas sensor biasing module is in the activated state and the electrochemical gas sensor biasing module is connected to the electrochemical gas sensor.

17. The electrochemical gas sensor biasing module of claim 11, wherein the battery is configured to deliver the biasing power to the electrochemical gas sensor when the electrochemical gas sensor is disconnected from a gas detector head.

18. An electrochemical gas sensor biasing module, comprising:
a main housing having a first end and a second end opposite the first end;
a sensor connector coupled to the main housing first end, the sensor connector including a plurality of connecting pins;
a battery coupled to the main housing second end;
an intrinsic safety circuit within the main housing and in communication with the battery and the sensor connector, the intrinsic safety circuit including a resistor and a fuse;
a low dropout regulator in communication with the battery and the sensor connector, the low dropout regulator being configured to output a constant voltage from the battery to the sensor connector; and
an on/off switch in communication with the battery, the on/off switch being configured to selectively transition the electrochemical gas sensor biasing module between an activated state and an deactivated state, the battery being configured to supply power to the sensor connector when the electrochemical gas sensor biasing module is in the activated state and to maintain the electrochemical gas sensor in a biased state when the electrochemical gas sensor biasing module is removably connected to the electrochemical gas sensor and the electrochemical gas sensor is unattached from a gas detector head.

19. The electrochemical gas sensor biasing module of claim 18, further comprising a first printed circuit board coupled to the main housing first end and a second printed circuit board coupled to the main housing second end.

20. The electrochemical gas sensor biasing module of claim 19, wherein:
the sensor connector and the low dropout regulator are coupled to the first printed circuit board; and
the battery, the resistor, and the fuse are coupled to the second printed circuit board.

* * * * *